United States Patent [19]

Perrin

[11] Patent Number: 5,420,140

[45] Date of Patent: May 30, 1995

[54] DIFLUORINATED QUINOLONES USEFUL FOR TREATING BACTERIAL INFECTIONS

[75] Inventor: Claude Perrin, Orsay, France

[73] Assignee: Bouchara S.A., France

[21] Appl. No.: 962,197

[22] PCT Filed: Apr. 10, 1992

[86] PCT. No.: PCT/FR92/00319

§ 371 Date: Dec. 8, 1992

§ 102(e) Date: Dec. 8, 1992

[87] PCT Pub. No.: WO92/18497

PCT Pub. Date: Oct. 29, 1992

[30] Foreign Application Priority Data

Apr. 10, 1991 [FR] France ................. 91 04472

[51] Int. Cl.⁶ .................. A61K 31/47; C07D 215/56
[52] U.S. Cl. ........................ 514/312; 546/156
[58] Field of Search .................. 546/156; 514/312

[56] References Cited

U.S. PATENT DOCUMENTS

| | | | |
|---|---|---|---|
| 4,398,029 | 8/1983 | Irikura et al. | 546/156 |
| 4,777,175 | 10/1988 | Culbertson et al. | 546/156 |
| 4,894,458 | 1/1990 | Masuzawa et al. | 546/156 |
| 4,997,943 | 3/1991 | Iwata et al. | 546/156 |
| 5,173,484 | 12/1992 | Petersen et al. | 546/156 |
| 5,328,908 | 7/1994 | Demuth, Jr. et al. | 514/312 |

FOREIGN PATENT DOCUMENTS 3-48678  3/1991  Japan .

*Primary Examiner*—Bernard Dentz
*Attorney, Agent, or Firm*—Bierman & Muserlian

[57] ABSTRACT

A method of treating bacterial infections in warm-blooded animals comprising administering to warm-blooded animals an antibactericidally effective amount of at least one compound of the formula

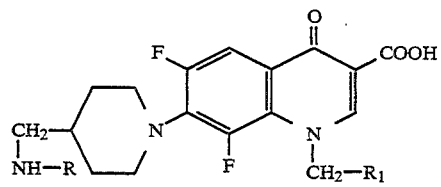

wherein R is

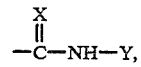

Y is selected from the group consisting of lower alkyl, lower alkenyl, phenyl optionally substituted with 1 to 3 members of the group consisting of halogen, lower alkyl, —NO₂, —CF₃ and alkoxy carbonyl, X is oxygen and R₁ is selected from the group consisting of methyl, fluoromethyl, vinyl, phenyl and

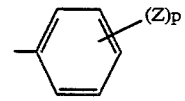

wherein Z is halogen and p is 1, 2 or 3 and its non-toxic, pharmaceutically acceptable salts with a base or acid.

5 Claims, No Drawings

DIFLUORINATED QUINOLONES USEFUL FOR TREATING BACTERIAL INFECTIONS

This application is a 371 of PCT/FR92/00319 filed Apr. 10, 1992.

This invention relates to the field of medicinal chemistry and more particularly to that of difluorinated quinolones.

More particularly it has as a subject matter difluoroquinolones which are substituted in position 7 with a piperidine ring.

Specifically it has as a subject matter the 7-(piperidinyl-1) 6,8-difluoro 4-oxo 1,4-dihydroquinoline 3-carboxylic acids of the general formula I

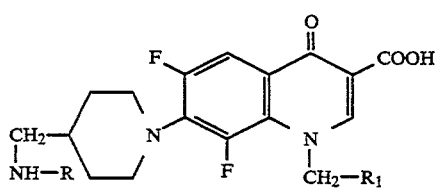

wherein R represents a hydrogen, a lower alkyl radical, a lower (hydroxy alkyl) radical, the acyl moiety of an organic carboxylic acid having from 1 to 10 carbon atoms or a carboxamido grouping of formula

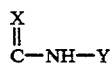

wherein Y is a lower alkyl radical, a lower alkenyl radical, a phenyl, or a substituted phenyl
and X is an oxygen or a sulphur
and $R_1$ represents a methyl radical, a fluoromethyl radical, a vinyl radical, a phenyl radical or a substituted phenyl radical of the formula

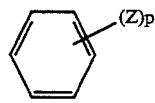

wherein Z represents a halogen atom
and p is equal to 1, 2 or 3.

Among the compounds of general formula I, it may more particularly cited:
the compounds for which $R_1$ is a methyl radical, having the formula $I_A$

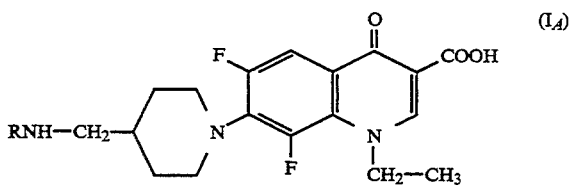

wherein R has the above-given definitions.
the compounds for which $R_1$ is a fluoromethyl radical, having the formula $I_B$

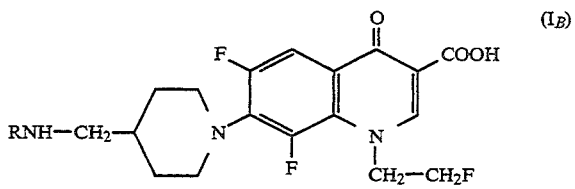

wherein R has the above-given definitions.
the compounds for which $R_1$ is a vinyl radical, having the formula $I_C$

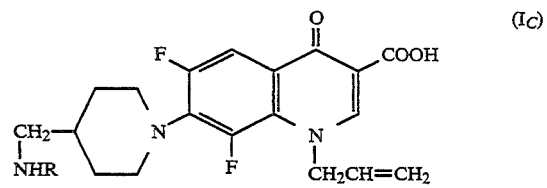

wherein R has the above-given definitions.
and
the compounds for which $R_1$ is a phenyl or substituted phenyl radical having the formula $I_D$

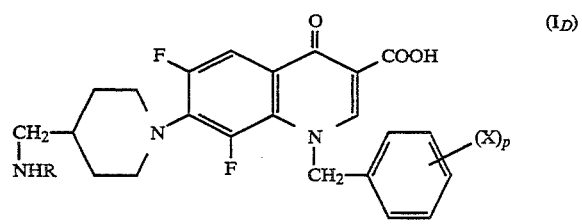

wherein R is defined as previously
X represents hydrogen or a halogen atom
and p is equal to 1, 2 or 3.

This invention also relates to the salts of the compounds of general formula I with a mineral or organic base. In fact the compounds of general formula I are very slightly soluble in water or in the aqueous medium such as the biological media. It appears thus wanted to increase their capacity to be dissolved and hence to their diffusion.

This invention also relates to the salts of the compounds of general formula I for which R is a hydrogen or a lower alkyl radical or a lower hydroxy alkyl radical with a mineral or organic acid, preferably a therapeutically-compatible acid.

Moreover the [4-aminomethyl piperidino] derivatives of general formula I show an asymmetric carbon atom

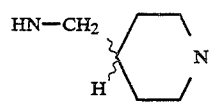

and may therefore be resolved into their optical isomers.

Among these salts of the compounds of general formula I with a mineral or organic base, it may more precisely cited the alkali metal salts, the earth-alkaline metal salts, the salts of iron, the salts of Aluminium, the salts of Magnesium and of the other non-toxic metals they may also be cited the alkylamine salts having from 1 to 6 carbon atoms, the salts of a hydroxyalkylamine, the salts of a cycloalkylamine, the salts of a (dicycloalkyl) amine, the salts of a di(cycloalkyl) alkylamine, the osamine salts, the basic amino acids salts, the quaternary ammonium salts, the phenyl alkylamine salts, the (heteroaryl) alkylamine salts, and the heteroarylamine salts.

Among these salts one prefers the alkali metal salts such as the sodium, the lithium or the ammonium salts, the alkylamine salts such as the methylamine salt, the ethylamine salt or the isopropylamine salt; the hydroxyalkylamine salts such as the amino ethanol or di(amino ethanol) salts or the tromethanol salts, the osamine salts such as the N-methyl glucamine salts, the basic amino acid salts such as the lysine salts, the arginine salts or the sarcosine salts as well as the quaternary ammonium salts such as choline or carnitine.

Among the addition salts with a mineral or organic acids, it may more particularly be cited the halohydrates such as the hydrochlorides, the hydrobromides, or the hydroiodides; the sulphates, the nitrates, the phosphates, the hypophosphites, or the metaphosphates; the salts of a carboxylic acid such as the acetates, the propionates, the lactates, the gluconates the benzoates, the salicylates, the gentisates, the thiophene carboxylates, or the indolyl acetates; the addition salts with a sulphonic acid such as a methane sulfonate, a trifluoromethane sulfonate, an ethane sulfonate, an isethionate, a camphosulphonate, a benzene sulphonate or a p.toluene sulphonate; the addition salts with a phosphonic or an organophosphoric acid such as glucose 1-phosphoric or glucose 1,6-diphosphoric acids.

Among the derivatives of general formula I for which R is the acyl moiety of an organic carboxylic acid, it may be cited the formyl, the acetyl, the propionyl, the pivaloyl, the benzoyl, the trimethoxy benzoyl, the dichlorobenzoyl or the naphtoyl derivatives.

The N-carboxamido derivatives are also of great biological interest namely as antibacterial agents, mainly the phenyl carboxamido derivatives i.e the compounds for which X is an oxygen and Y is a substituted or unsubstituted phenyl radical.

When Y is a substituted phenyl, it may carry from 1 to 3 substituents selected from the group consisting of a halogen, a lower alkyl radical, a nitro group, an alkoxycarbonyl group, and a trifluoromethyl.

Out of these substituents the halogens—chlorine or fluorine—and the nitro group are those most interesting as regard to the antibacterial activity.

This invention also encompasses a process for producing the compounds of general formula I which consists in reacting a 6,7,8-trifluoroquinolone of general formula II

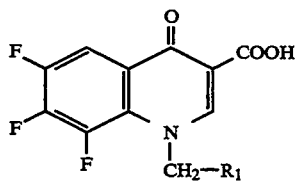

wherein $R_1$ has the above-given definitions with a (4-aminomethyl) piperidine of general formula III

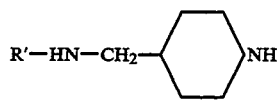

wherein R' is a hydrogen, a lower alkyl radical or an acyl moiety which is easily split in an inert solvent to produce a 7-aminomethyl quinolone of general formula IV

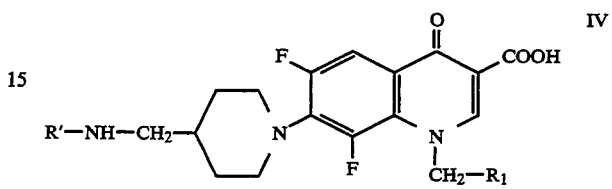

wherein $R_1$ and R' are defined as previously
which may —when desired— be salified by adding a mineral or organic acid
or acylated when R' is a hydrogen or a lower alkyl radical, by reaction with a functional derivative of an organic carboxylic acid such as a chloride, an anhydride or a mixed anhydride
or submitted to a carbonatation by reaction with an alkyl or aryl isocyanate or isothiocyanate to produce an Urea or a Thiourea or salified by adding a mineral or organic base.

The aminating reaction in which a trifluoroderivative of general formula II is reacted with an aminomethyl piperidine of general formula III is a complex reaction which requires the selection of a quite inert solvent. In fact the fluorine atom in position 7 is extremely labile and reacts indifferently with whichever reactant, aminated solvent or with an alkanol concurrently with the aminomethyl piperidine. It is thus compulsory to limit at the lowest degree the side reactions —to use very polar solvents such as dimethyl sulfoxide, pyridine, hexaphosphorotriamide or chemically-inert solvents such as Dioxane, isopropylether, in the presence of a non-reactive tertiary base such as triethylamine or pyridine.

The reaction is carried out by heating —and preferably— at a temperature ranging from 100° to 150° C. Pyridine or the pyridine bases such as collidine or lutidine are the presently preferred solvents of the reaction.

The compounds of general formula I show interesting biological activities and namely very marked antibacterial properties. They show antibacterial properties against a broad range of strains, as well gram positive and gram negative. Moreover the compounds of the structure Carboxamido evidence antibacterial properties against Gram positive bacterias quite unusual, mainly against staphylococci strains which are resistant to all the antibiotics.

For these reasons the compounds of general formula I find a use as active ingredient in pharmaceutical compositions.

This invention then includes the pharmaceutical compositions containing as an active ingredient, at least one compound of general formula I or an addition salt thereof with a mineral or organic base in admixture or conjunction with an inert, non-toxic, pharmaceutically-acceptable carrier or vehicle. The pharmaceutical compositions according to this invention are intended to the parenteral, digestive, topical, permucous or percutaneous ways of administration. Particularly for the parenteral use, the compositions of this invention are offered in the form of injectible solutes, or suspensions in an aqueous or oily vehicle and packed in ampules, in multidosis flasks, in auto-injectible syringes or in unidosis bottles.

For the administration by digestive way, the compositions of this invention are offered in the form of uncoated tablets, coated or covered by a film, tablets, soft gelatin capsules, lozenges, pills, sachets of powder which may be flavoured, sweetened or coloured, syrups, emulsions or gels.

For the topical application the compositions according to this invention are offered in the form of ear drops, nose drops, eye drops, powders for auricular insufflation, gels, creams, lotions or salves.

For the percutaneous application, the active ingredient is dissolved or dispersed in a vehicle containing a polar solvent such as benzylic alcohol, or dimethyl sulfoxide, in addition to a penetration enhancer such as lauroylcholine or fusidic acid.

For the use as antibacterial, namely for treating the septicemias, pneumopathias, or urinary, or genital infections, the unitary dosology ranges from 0.100 to 0.400 g and the daily dosage may vary from 0.200 g to 0.600 g.

The following examples illustrate the invention. They do not limit it in any manner.

EXAMPLE I 7-(4-aminomethyl piperidinyl-1) 6,8-difluoro 1-ethyl 4-oxo 1,4-dihydroquinoleinyl-3 carboxylic acid (Compound 1)

1,25 g 6,7,8-trifluoro 1-ethyl 4-oxo 1,4-dihydroquinoleinyl-3 carboxylic acid are dissolved in 10 ml dimethylformamide and to the resulting solution 1,45 g of 4-aminomethyl piperidine are added. The reaction mixture is heated to 140° C. for 4 hours then after return to room temperature it is diluted with water until crystallization starts.

After one hour at 0° C. under stirring, the crystals are separated which are dried, washed with water until neutral then with ethanol and further perfectly dried under reduced pressure.

They are thus obtained 1,4 g of the desired piperidino derivative which is recrystallized for analysis from ethanol. It is thus recovered 1,1 g of pure compound melting on the Koffler's block at 260°–261° C.

The 7-(4-aminomethyl piperidinyl-1) 6,8-difluoro 1-ethyl 4-oxo 1,4-dihydroquinoleinyl-3 carboxylic acid has been converted into its hydrochloride (Compound Ia) by adding some hydrochloric acid to a tetrahydrofuranic solution (MP=260° C.) and into its methane sulphonate (Compound Ib) by adding methane sulphonic acid (MP>260° C.).

EXAMPLE II 7-(4-(3-hydroxypropionyl aminomethyl)piperidinyl-1) 6,8-difluoro 1-ethyl 4-oxo 1,4-dihydroquinoleinyl-3 carboxylic acid (Compound II)

1,7 g of 7-(4-aminomethyl piperidinyl-1) 6,8-difluoro 1-ethyl 4-oxo 1,4-dihydroquinoleinyl-3 carboxylic acid are dissolved in 20 ml pyridine and 5 ml triethylamine. To this solution one gradually adds 0,9 g β-hydroxypropionic acid chloride and the whole mixture is kept under stirring for 4 hours at room temperature and then diluted with 20 ml of a saturated aqueous solution of sodium bicarbonate while maintaining the stirring for a further hour.

The thus formed crystals are succion filtered, they are dried then washed with water and finally with ethanol. One dries under vaccuum. They are thus obtained 1.05 g of the β-hydroxypropionylamide melting above 260° C.

EXAMPLE III 7-(4-aminomethyl piperidinyl-1) 6,8-difluoro 1-fluoroethyl 4-oxo 1,4-dihydroquinoleinyl-3 carboxylic acid (Compound III)

Operating as in example I but starting from 6,7,8-trifluoro 1-fluoroethyl 4-oxo 1,4-dihydroquinoleinyl-3 carboxylic acid, one obtains 7-(4-aminomethyl piperidinyl-1) 6,8-difluoro 1-(fluoroethyl) 4-oxo 1,4-dihydroquinoleinyl-3 carboxylic acid which melts at 250° C. The IR spectrum and the elemental analysis are in accordance with the structure.

EXAMPLE IV 7-(4-aminomethyl piperidinyl-1) 6,8-difluoro 1-(4-fluorobenzyl) 4-oxo 1,4-dihydroquinoleinyl-3 carboxylic acid (Compound IV)

Operating as in example I but starting from 6,7,8-trifluoro 1-(4-fluorobenzyl) 4-oxo 1,4-dihydroquinoleinyl-3 carboxylic acid, one obtains 7-(4-aminomethyl piperidinyl-1) 6,8-difluoro 1-(4-fluorobenzyl) 4-oxo 1,4-dihydroquinoleinyl-3 carboxylic acid melting at 256° C. In the same manner it is possible to obtain 7-(4-aminomethyl piperidinyl-1) 6,8-difluoro 1-(2-chlorobenzyl) 4-oxo 1,4-dihydroquinoleinyl-3 carboxylic acid, which melts above 260° C. (Compound V).

EXAMPLE V 7-(4-aminomethyl piperidinyl-1) 6,8-difluoro 1-allyl 4-oxo 1,4-dihydroquinoleinyl-3 carboxylic acid (Compound VI)

Using the same method as in example I, but starting from 6,7,8-trifluoromethyl 1-allyl 4-oxo 1,4-dihydroquinoleinyl-3 carboxylic acid it is obtained 7-(4-aminomethyl piperidinyl-1) 6,8-difluoro 1-allyl 4-oxo 1,4-dihydroquinoleinyl-3 carboxylic acid which melts at 245° C.

EXAMPLE VI

7-[(4-propionylaminomethyl)piperidinyl-1] 6,8-difluoro 1-ethyl 4-oxo 1,4-dihydroquinoleinyl-3 carboxylic acid (Compound VII)

By reacting compound of example I dissolved into pyridine with propionyl chloride, the propionylaminomethylated derivative is obtained which melts at 260° C.

In the same fashion 7-[(4-propionyl aminomethyl)-piperidinyl-1] 6,8-difluoro 1-fluoroethyl 4-oxo 1,4-dihydroquinoleinyl-3 carboxylic acid which melts at 260° C. (Compound VIII).

In the same fashion 7-(4-acetylamino piperidinyl-1) 6,8-difluoro 1-allyl 4-oxo 1,4-dihydroquinoleinyl-3 carboxylic acid is obtained which melts at 260° C. (Compound IX).

EXAMPLE VII

7-[(4-Phenylamino carboxamidomethyl)piperidinyl-1] 6,8-difluoro 1-ethyl 4-oxo 1,4-dihydroquinoleinyl-3 carboxylic acid (Compound X)

1,2 g of 7-(4-aminomethylpiperidinyl-1) 6,8-difluoro 1-ethyl 4-oxo 1,4-dihydroquinoleinyl-3 carboxylic acid is dissolved in 25 ml dimethyl formamide and to the solution they are added under cooling at 0° with a ice bath, 1,25 g phenyl isocyanate previously dissolved in 2 ml tetrahydrofuran. The addition is gradually performed under vigorous stirring.

After achievement of the addition, the reaction mixture is heated to the reflux temperature and the heating is kept for 5 hours. One lets then revert to room temperature and the resulting phenylurea precipitates by cooling. On lets stand in the ice bath for one hour then separates the crystalis by filtration. They are dried washed with ethanol then with water and perfectly dried under vaccuum. 1,25 g of the phenylurea are thus recovered which melts above 260° C.

In the same manner 7-[(4-benzoylaminocarboxamido methyl)piperidinyl-1] 6,8-difluoro 1-allyl 4-oxo 1,4-dihydroquinoleinyl-3 carboxylic acid is prepared which melts at 262° C. (Compound XI).

EXAMPLE VIII

In the same manner the following ureas have been prepared:

7-[(4-(4-methylphenylamino carbonylaminomethyl)-piperidinyl-1] 6,8-difluoro 1-ethyl (Compound XII) F>260° C.

7-[4-(3-fluorophenyl)aminocarbonyl aminomethyl piperidinyl-1] 6,8-difluoro 1-ethyl (Compound XIII) F=264° C.

7-[4-(3,4-dichlorophenyl)aminocarbonyl aminomethyl piperidinyl-1] 6,8-difluoro 1-ethyl (Compound XIV) F=220° C.

7-[4-(4-ethoxycarbonylphenyl)aminocarbonyl aminomethyl piperidinyl-1] 6,8-difluoro 1-ethyl (Compound XV) F=252° C.

7-[4-(4-methoxyphenyl)aminocarbonyl aminomethyl piperidinyl-1] 6,8-difluoro 1-ethyl (Compound XVI) F>260° C.

7-[4-(4-nitrophenyl)aminocarbonyl aminomethyl piperidinyl-1] 6,8-difluoro 1-ethyl (Compound XVII) F=222° C.

7-[4-(2,4-difluorophenyl)aminocarbonyl aminomethyl piperidinyl-1] 6,8-difluoro 1-ethyl (Compound XVIII) F=262° C.

7-[4-(2-fluorophenyl)aminocarbonyl aminomethyl piperidinyl-1] 6,8-difluoro 1-ethyl (Compound XIX) F>260° C.

EXAMPLE IX

Production of 7-[(4-allylaminocarbonyl aminomethyl)piperidinyl-1] 6,8-difluoro 1-ethyl 4-oxo 1,4-dihydroquinoleinyl-3 carboxylic acid 1,20 g 7-(4-aminomethyl piperidinyl-1) 6,8-difluoro 1-ethyl 4-oxo 1,4-dihydroquinoleinyl-3 carboxylic acid are dissolved in 20 ml dimethyl sulphoxide and the solution is cooled to 5° C. While maintaining this solution at the same temperature in a water-ice bath, it is added dropwise a solution 0.7 g allyl isocyanate in dimethylsulphoxide. The solution is kept under the same temperature under stirring for one hour, then is let to revert to room temperature.

The excess of reagent is destroyed by adding an aqueous diluted solution of sodium hydroxide. After stirring the precipitate of Urea is separated, dried, Washed with water then with ethanol at 70%. The allylurea has a melting point of 241° C.

In the same manner 7-[(4-allylaminothiocarbonyl aminomethyl)piperidinyl-1] 6,8-difluoro 4-oxo 1,4-dihydroquinoleinyl-3 carboxylic acid is prepared (MP=255° C.).

In the same manner but starting from 7-(4-aminomethyl piperidinyl-1) 6,8-difluoro 1-allyl 4-oxo 1,4-dihydroquinoleinyl-3 carboxylic acid, 7-[(4-allylaminocarbonyl aminomethyl)piperidinyl-1] 6,8-difluoro 1-allyl 4-oxo 1,4-dihydroquinoleinyl-3 carboxylic acid is obtained. This allylurea melts at 238°-240° C.

The corresponding allyl thio Urea is also prepared using allyl isothiocyanate. The allyl thio Urea melts at 250°-251° C.

EXAMPLE X

Tablets of 7-(4-aminomethyl piperidinyl-1) 6,8-difluoro 1-ethyl 4-oxo 1,4-dihydroquinoleinyl-3 carboxylic acid as the hydrochloride at 250 mg

| | |
|---|---|
| 7-(4-aminomethylpiperidinyl-1) 6,8-difluoro 1-ethyl 4-oxo 1,4-dihydroquinoleinyl-3 carboxylic acid as the hydrochloride | 250 g |
| Maïs starch | 40 g |
| Corn starch | 40 g |
| Carboxymethyl starch | 20 g |
| Polyvinylpyrolidone sold under the Trade Name "Polyvidone excipient" | 10 g |
| Microcrystalline Cellulose | 30 g |
| Magnesium stearate | 10 g | for 1000 tablets achieved at a mean weight of 0.400 g

EXAMPLE XI

Eye drops based on 7-(4-aminomethyl piperidinyl-1) 6,8-difluoro 1-ethyl 4-oxo 1,4-dihydroquinoleinyl-3 carboxylic acid as the hydrochloride

| | |
|---|---|
| Active ingredient | 10 g |
| Disodium Tetracemate | 0.1 g |
| Disodium Phosphate | 0.05 g |
| Monosodium Phosphate | 0.04 g |
| Sodium Hypophosphite | 0.02 g |
| Methyl Paraben | 0.015 g |
| Distilled water enough for | 100 ml |

Each drop contains 0.005 g of active ingredient.

EXAMPLE XII

Determination of the antibacterial activity of the compounds of this invention

Material and methods

The compound have been tested towards 7 reference strains:

4 species Gram positive:
  Bacillus subtilis ATCC 9372
  Staphylococcus aureus ATCC 25923
  Streptococcus faecalis ATCC 8043
  Staphylococcus aureus CB 951

3 species Gram negative:
  Escherichia coli ATCC 25922
  Pseudomonas aeruginosa ATCC 22853
  Acinetobacter calcoaceticus (Var.anitratum) ATCC 17903

The determination of minimal inhibitory concentrations (MIC) has been performed using a microdution method (microplates and inoculator Dynatech) in liquid medium (MUELLER-HINTON broth) under a volume of 100 μl and for a range of concentrations from 128 to 0.06 mg/l, prepared from a mother liquor of antibiotics titrating 512 mg/l. The preparation of these mother liquors has been performed and vary depending on the molecules as a function of the solubility criterions. Inoculation has been done by adding in each will, 10 μl of a dilution in saline of 18 hours old broth in a brain-heart broth, such as each well contains about $10^6$ bacterias/ml.

The Minimal Inhibitory Concentrations are read as the first concentration of antibiotic which will not give a growth macroscopically detectable after 18 hours incubating at 37°.

boxyl, X is oxygen or and $R_1$ is selected from the group consisting of methyl, fluoromethyl, vinyl, phenyl and

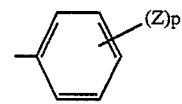

wherein Z is a halogen and p is 1, 2 or 3 and its non-toxic, pharmaceutically acceptable salts with a base or acid.

2. A method of treating bacterial infections in warm-blooded animals comprising administering to warm-blooded animals an antibactericidally effected amount of at least one compound of the formula

TABLE

Minimal inhibitory (MIC) and Minimal bactericidal concentrations (MBC) (in μg/ml)

| Bacterial Species Products | Bacillus Subtilis ATCC 9372 | | S. aureus ATCC 25923 | | S. faecalis ATCC 8043 | | E. coli ATCC 25922 | | P. aeruginosa ATCC 22853 | | Acinetobacter Baumanii ATCC 17904 | | S. aureus CB-951 (1) | |
|---|---|---|---|---|---|---|---|---|---|---|---|---|---|---|
| | MIC | MBC | MIC | MBC | MIC | MBC | MIC | MBC | MIC | MBC | MIC | MBC | MIC | MBC |
| Compound 1 | 0,25 | 0,25 | 0,25 | 0,25 | 0,5 | 0,5 | 0,5 | 0,5 | 2 | 4 | 0,25 | 0,5 | 2 | 2 |
| Compound a | | | 0,25 | 0,25 | 0,5 | 0,5 | 0,5 | 0,5 | 2 | 4 | 0,25 | 0,25 | 2 | 2 |
| Compound b | | | 0,5 | 0,5 | 0,5 | 1 | 0,5 | 0,5 | 4 | 8 | 0,5 | 0,5 | 4 | 4 |
| Compound 2 | | | 0,5 | 1 | 4 | 4 | 8 | 8 | >32 | >32 | 2 | 4 | 4 | 4 |
| Compound 3 | | | 0,5 | 1 | 2 | 4 | 2 | 2 | 8 | 16 | 2 | 4 | 4 | 8 |
| Compound 4 | | | 12 | 12 | >12 | 12 | >12 | >12 | >12 | >12 | 12 | >12 | >12 | 12 |
| Compound 5 | | | 2 | 4 | 16 | >16 | 4 | 8 | >16 | >16 | 4 | 8 | >16 | >16 |
| Compound 6 | 1 | 2 | 1 | 2 | 1 | 4 | 1 | 2 | 8 | 16 | 1 | 2 | 32 | 64 |
| Compound 7 | | | 0,5 | 0,51 | 8 | 8 | 8 | 8 | >16 | >16 | 0,25 | 0,5 | 1 | 1 |
| Compound 8 | | | 0,15 | 0,3 | 6 | >12 | 6 | >12 | >12 | >12 | 0,3 | 0,7 | 0,3 | 0,7 |
| Compound 9 | 1 | 2 | 1 | 4 | 4 | 16 | 16 | 32 | >128 | >128 | 4 | 8 | 4 | 8 |
| Compound 10 | | | 0,15 | 0,3 | 25 | >25 | 0,7 | 0,7 | 3 | 6 | 0,3 | 0,7 | 0,3 | 1,5 |
| Compound 11 | 0,5 | 1 | 1 | 4 | 16 | 32 | 128 | >128 | 128 | >128 | 1 | 4 | 4 | 4 |
| Compound 12 | | | 0,06 | 0,06 | 4 | 4 | >16 | >16 | >16 | >16 | 0,06 | 0,06 | 0,25 | 1 |
| Compound 13 | | | 0,12 | 0,25 | >16 | >16 | >16 | >16 | >16 | >16 | 0,06 | 0,06 | 0,25 | 0,5 |
| Compound 14 | | | 2 | 8 | >16 | >16 | >16 | >16 | >16 | >16 | 4 | 8 | 16 | >16 |
| Compound 15 | | | 0,12 | 0,12 | >16 | >16 | >16 | >16 | >16 | >16 | 0,12 | 0,25 | 1 | 2 |
| Compound 16 | | | 0,06 | 0,06 | 8 | 16 | 16 | 16 | >16 | >16 | 0,06 | 0,03 | 0,5 | 1 |
| Compound 17 | | | 0,03 | 0,03 | 4 | 8 | 16 | >16 | >16 | >16 | ≦0,007 | ≦0,007 | 1 | 1 |
| Compound 18 | | | ≦0,12 | ≦0,12 | 2 | 2 | 2 | 4 | >16 | >16 | ≦0,12 | ≦0,12 | 0,25 | 0,25 |
| Compound 19 | | | 0,007 | 0,015 | 2 | 2 | 8 | 8 | >32 | >32 | 0,003 | 0,003 | 0,03 | 0,06 |
| Pefloxacine | | | 0,12 | 0,25 | 1 | 1 | 0,06 | 0,06 | 2 | 2 | 0,06 | 0,06 | 4 | 4 |
| Ciprofloxacine | | | 0,25 | 0,25 | 0,25 | 0,25 | 0,007 | 0,007 | 0,12 | 0,25 | 0,06 | 0,06 | 4 | 4 |

(1) Methicillino resistant, Erythromycino-lincomycino resistant, pefloxacino resistant

What is claimed is:

1. A compound selected from the group consisting of 7-(piperidinyl) 6,8-difluoro 4-oxo 1,4-dihydroquinolinyl-3 carboxylic acid of the formula I

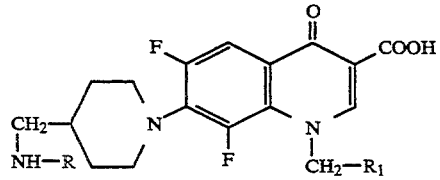

wherein R is

wherein Y is selected from the group consisting of lower alkyl, lower alkenyl, phenyl optionally substituted with 1 to 3 members of the group consisting of halogen, lower alkyl, —$NO_2$, —$CF_3$ and alkoxy car-

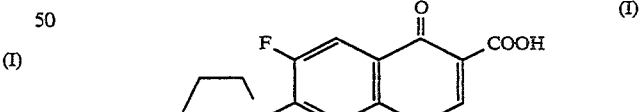

wherein R is

Y is selected from the group consisting of lower alkyl, lower alkenyl, phenyl optionally substituted with 1 to 3 members of the group consisting of halogen, lower alkyl, —$NO_2$, —$CF_3$ and alkoxy carbonyl, X is oxygen and $R_1$ is selected from the group consisting of methyl, fluoromethyl, vinyl, phenyl and

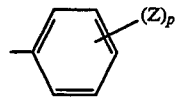
wherein X is halogen and p is 1, 2 or 3 and its non-toxic, pharmaceutically acceptable salts with a base or acid.
3. The method of claim 2 wherein the active compound has the formula
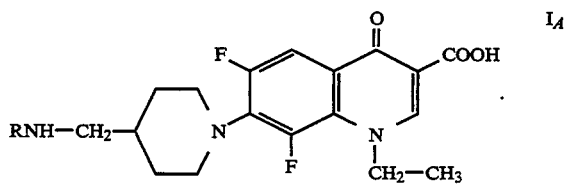
4. The method of claim 2 wherein $R_1$ is —$CH_2F$.
5. The method of claim 2 wherein $R_1$ is —$CH=CH_2$.
* * * * *